United States Patent [19]

Maurer et al.

[11] 4,014,998
[45] Mar. 29, 1977

[54] O-ALKYL-S-(2-(1,1,2-TRIFLUORO-2-CHLOROETHYLMERCAPTO)-ETHYL)(THIONO)(DI) THIOLPHOSPHORIC (PHOSPHONIC) ACID ESTERS AND ESTER-AMIDES AND PESTICIDAL USE

[75] Inventors: Fritz Maurer; Hans-Jochem Riebel, both of Wuppertal; Ingeborg Hammann, Cologne; Wolfgang Behrenz, Overath-Steinenbrueck; Bernhard Homeyer, Leverkusen, all of Germany

[73] Assignee: Bayer Aktiengesellschaft, Leverkusen, Germany

[22] Filed: Feb. 19, 1976

[21] Appl. No.: 659,610

[30] Foreign Application Priority Data

Mar. 8, 1975  Germany .................... 2510138

[52] U.S. Cl. .................... 424/216; 260/948
[51] Int. Cl.² .................... A01N 9/36; C07F 9/165; C07F 9/40; C07F 9/24
[58] Field of Search .................... 260/948; 424/216

[56] References Cited
UNITED STATES PATENTS 3,150,162  9/1964  Schrader .................... 260/948 X
3,277,215  10/1966  Schrader et al. .................... 260/948
3,743,687  7/1973  Schrader et al. .................... 260/948

*Primary Examiner*—Richard L. Raymond
*Attorney, Agent, or Firm*—Burgess, Dinklage & Sprung

[57] ABSTRACT

O-Alkyl-S-[2-(1',1',2'-trifluoro-2'-chloroethylmercapto)-ethyl](thiono)(di)thiolphosphoric (phosphonic) acid esters and ester-amides of the formula

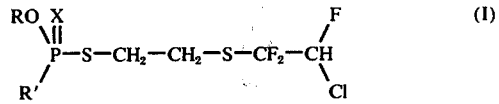

in which
R is alkyl with 1 to 6 carbon atoms,
R' is alkyl, alkoxy, alkylmercapto or alkylamino with 1 to 6 carbon atoms in each alkyl moiety, amino or phenyl, and
X is oxygen or sulfur, which possess arthropodicidal and nematicidal properties.

10 Claims, No Drawings

O-ALKYL-S-(2-(1,1,2-TRIFLUORO-2-CHLOROETHYLMERCAPTO)-ETHYL)(THIONO)(DI) THIOLPHOSPHORIC (PHOSPHONIC) ACID ESTERS AND ESTER-AMIDES AND PESTICIDAL USE

The present invention relates to and has for its objects the provision of particular new O-alkyl-S-[2-(1',1', 2'-trifluoro-2'-chloroethylmercapto)-ethyl](thiono)(di)thiolphosphoric(phosphonic) acid esters and ester-amides, which possess arthropodicidal and nematicidal properties, active compositions in the form of mixtures of such compounds with solid and liquid dispersible carrier vehicles, and methods for producing such compounds and for using such compounds in a new way especially for combating pests, e.g., arthropods and nematodes, with other and further objects becoming apparent from a study of the within specification and accompanying examples.

It is known from German Pat. specification No. 917,668 and German published specifications DAS No. 1,010,960, 1,014,987, 1,087,591 and 1,153,568 that S-alkylmercaptoethyl(thiono) thiolphosphoric acid esters, for example O,O-dimethyl-S-(1-N-methylcarbamoylethylmercapto)-ethyl-thiol-(Compound A) or O,O-diethyl-S-ethylmercaptoethyl-thionothiolphosphoric acid ester (Compound B) possess insecticidal and acaricidal properties.

The present invention provides S-(trifluorochloroethylmercapto)ethyl(thiono)(di)thiolphosphoric(phosphonic) acid esters and ester-amides of the general formula

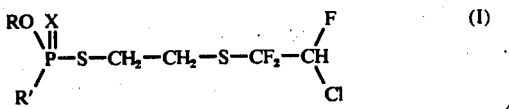

in which
R is alkyl with 1 to 6 carbon atoms,
R' is alkyl, alkoxy, alkylmercapto or alkylamino with 1 to 6 carbon atoms in each alkyl moiety, amino or phenyl, and
X is oxygen or sulfur, The compounds of the formula (I) have been found to possess excellent arthropodicidal (especially leaf-insecticidal, soil-insecticidal and acaricidal) and nematicidal properties.

Preferably, R is straight-chain or branched alkyl with up to 5, especially 1 to 4, carbon atoms, and R' is straight-chain or branched alkyl, alkoxy, alkylmercapto or alkylamino with up to 5, especially 1 to 4, carbon atoms in each alkyl moiety, amino or phenyl.

Surprisingly, the S(trifluorochloroethylmercapto)-ethyl(thiono)(di)thiolphosphoric(phosphonic) acid esters and ester-amides according to the invention possess a better leaf-insecticidal and soil-insecticidal, acaricidal and nematicidal action than the nearest compounds of analogous structure and of the same type of action known from the state of the art. The compounds according to the invention are not only active against insects, mites and nematodes which damage plants, but also against pests harmful to health and pests of stored products. They thus represent a genuine enrichment of the art.

The invention also provides a process for the preparation of an S-(trifluorochloroethylmercapto)-ethyl (thiono)(di)thiolphosphoric(phosphonic) acid ester or ester-amide of the formula (I), in which a (thiono)(di)-thiolphosphoric(phosphonic) acid ester derivative or ester-amide derivative of the general formula

in which
R, R' and X have the above-mentioned meanings, and
M is hydrogen or one equivalent of an alkali metal, alkaline earth metal or ammonium, is reacted with a trifluorochloroethyl-β-halogenoethyl-thioether of the general formula

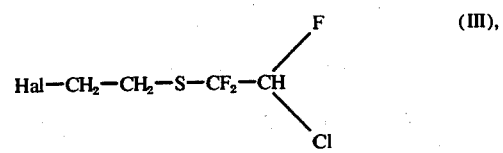

in which
Hal is halogen, preferably bromine,
if appropriate in the presence of an acid acceptor and, if appropriate, in the presence of a solvent or diluent.

If, for example, the potassium salt of O-ethylpropane-thionothiolphosphonic acid ester and 1,1,2-trifluoro-2-chloro-2'-bromodiethyl thioether are used as starting materials, the course of the reaction can be represented by the following equation:

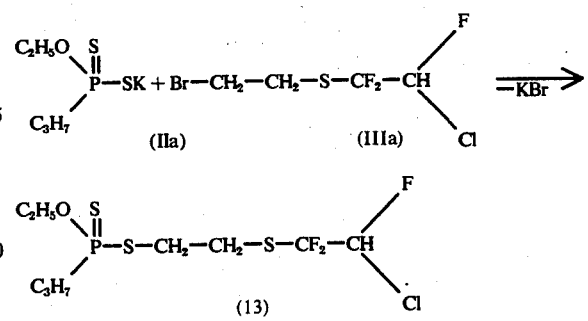

The (thiono)(di)thiolphosphoric(phosphonic) acid ester derivatives and ester-amide derivatives of the formula (II) are known from the literature and can be prepared according to generally customary processes for example, German published specifications DAS Nos. 1,141,634 and 1,164.408.

The trifluorochloroethyl-β-halogenoethyl-thioethers of the formula (III) can be obtained, for example, by reaction of 1,1,2-trifluoro-2-chloro-2'-hydroxy-diethyl-sulfide (prepared according to K. E. Rapp et al., J. Amer. Chem. Soc. 72 (1950), page 3644) with phosphorus trihalides in accordance with the following equation:

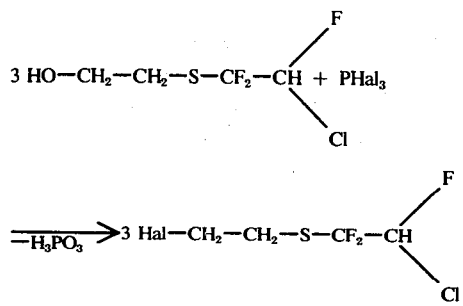

$$\xrightarrow{-H_3PO_3} 3\ \text{Hal}-CH_2-CH_2-S-CF_2-CH\diagup^{F}_{Cl}$$

The following may be mentioned as examples of (thiono)(di)thiolphosphoric(phosphonic) acid ester derivatives and ester-amide derivatives (II) to be used in accordance with the process: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O,O-di-tert.-butyl-, O-ethyl-O-n-propyl-, O-ethyl-O-isopropyl-, O-ethyl-O-n-butyl-, O-ethyl-O-sec.-butyl-, O-ethyl-O-tert.-butyl-, O-methyl-O-ethyl-, O-methyl-O-n-propyl-, O-methyl-O-isopropyl, O-methyl-O-n-butyl-, O-methyl-O-sec.-butyl-, and O-methyl-O-tert.-butylthiolphosphoric acid diesters, the corresponding alkali metal salts, alkaline earth metal salts or ammonium salts and, in each case the thiono analogues; O,S-dimethyl-, O,S-diethyl-, O,S-di-n-propyl-, O,S-di-isopropyl-, O,S-di-n-butyl-, O,S-di-sec.-butyl-, O,S-di-isobutyl-, O,S-di-tert.-butyl, O,S-di-pentyl-, O-ethyl-S-n-propyl-, O-ethyl-S-n-butyl-, O-ethyl-S-sec.-butyl-, O-ethyl-S-tert.-butyl-, O-propyl-S-ethyl- and O-isopropyl-S-ethyldithiolphosphoric acid diester, the corresponding alkali metal, alkaline earth metal and ammonium salts and, in each case, the corresponding thiono analogues; O-methyl-, O-ethyl-, O-n-propyl-, O-isopropyl-, O-n-butyl-, O-isobutyl-, O-sec.-butyl-, O-tert.-butyl- and O-pentyl-methane-, -ethane-, -n-propane-, -isopropane- and -phenyl-thiolphosphonic acid ester, the corresponding alkali metal, alkaline earth metal and ammonium salts and, in each case, the corresponding thiono analogues; and O-methyl-N-methyl-, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-n-propyl-N-n-butyl-, O-isopropyl-N-ethyl-, O-isopropyl-N-n-butyl-, O-pentyl-N-ethyl-, O-pentyl-N-n-propyl-, O-isopropyl-N-sec.-butyl-, O-isopropyl-N-tert.-butyl- and O-isopropyl-N-pentyl-thiolphosphoric acid ester-amide, the corresponding alkali metal, alkaline earth metal and ammonium salts and, in each case, the corresponding thiono analogues, as well as the unsubstituted amides.

An example of the trifluorochloroethyl-β-halogenoethyl thioethers to be reacted in accordance with the process is 1,1,2-trifluoro-2-chloro-2'-bromodiethyl thioether.

The process for the preparation of the compounds according to the invention is preferably carried out in the presence of a suitable solvent or diluent. Practically all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as the acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, trimethylamine, dimethylaniline, dimethylbenzylamine and pyridine.

The reaction temperature can be varied within a fairly wide range. In general, the reaction is carried out at between 0° and 100° C, preferably at from 35° to 50° C.

The reaction is in general allowed to take place under normal pressure.

To carry out the process, the starting materials are preferably employed in equimolar amounts. An excess of one or other reactant produces no essential advantages. The reaction is preferably carried out in one of the stated solvents, in most cases at elevated temperature. After completion of the reaction, an organic solvent, for example toluene, is generally added to the reaction mixture, the layers are separated and the organic phase is worked up in the usual manner by washing, drying and distilling off the solvent.

The new compounds are obtained in the form of oils which in most cases cannot be distilled without decomposition but can be freed from the last volatile constituents by so-called "slight distillation," that is to say by prolonged heating under reduced pressure to moderately elevated temperatures, and can be purified in this way. They are characterized by the refractive index.

As has already been mentioned, the S-(trifluorochloroethylmercapto)-ethyl(thiono)(di)thiolphosphoric(phosphonic) acid esters and ester-amides according to the invention are active against arthropod and nematode pests; in particular, they are distinguished by an excellent leaf-insecticidal, soil-insecticidal, acaricidal and nematicidal activity. Furthermore, they combine a low phytotoxicity with a good action both against sucking and biting insects and against mites.

For this reason, the compounds according to the invention can be employed successfully as pesticides in plant protection and in the hygiene field and the field of protection of stored products.

The active compounds according to the invention are well tolerated by plants and have a favorable level of toxicity to warm-blooded animals, and can be used for combating all or individual stages of development, including the pre-embryonic, normally sensitive and resistant, stages of development of arthropods and nematodes where these are known as pests in agriculture, in forestry, in the protection of stored products and materials, and in hygiene.

The economically important pests in agriculture and forestry, as well as pests of stored products, material pests and pests harmful to health, include: from the class of the Isopoda, for example, *Oniscus asellus*, *Armadillidium vulgare* and *Porcellio scaber*; from the class of the Diplopoda, for example *Blaniulus guttulatus*; from the class of the Chilopoda, for example *Geophilus carpophagus* and *Scutigera* spec.; from the class of the Symphyla, for example *Scutigerella immaculata*; from the class of the Arachnida, for example, *Scorpio maurus* and *Latrodectus mactans;* from the order of the Acarina, for example *Acarus siro, Argas reflexus, Ornithodoros moubata, Dermanyssus gallinae, Eriophyes ribis, Phyllocoptruta oleivora, Boophilus microplus, Rhipicephalus evertsi, Sarcoptes scabiei, Tarsonemus* spec., *Bryobia praetiosa, Panonychus citri, Panonychus ulmi, Tetranychus tumidus* and *Tetranychus urticae;* from the order of the Thysanura, for example, *Lepisma saccharina;* from the order of the Collembola, for example *Onychiurus armatus;* from the order of the Orthoptera, for example, *Blatta orientalis, Periplaneta americana, Leucophaea maderae, Blattella germanica, Acheta domesticus, Gryllotalpa* spec., *Locusta migratoria migratorioides, Melanoplus differentialis* and *Schistocerca gregaria;* from the order of the Dermaptera, for example, *Forficula auricularia;* from the order of the Isoptera, for example, *Reticulitermes* spec.; from the order of the Anoplura, for example, *Phylloxera vastatrix, Pemphigus* spec. and *Pediculus humanus corporis;* from the order of the Thysanoptera, for example, *Hercinothrips femoralis* and *Thrips tabaci;* from the order of the Heteroptera, for example, *Eurygaster* spec., *Dysdercus intermedius, Piesma quadrata, Cimex lectularius, Rhodnius prolixus* and *Triatoma* spec.; from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus cerasi, Myzus persicae, Phorodon humuli, Rhopalosiphum padi, Empoasca* spec., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spec. and *Psylla* spec.; from the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spec., *Bucculatrix thurberiella, Phyllocnistis citrella, Agrotis* spec., *Euxoa* spec., *Feltia* spec., *Earias insulana, Heliothis* spec., *Laphygma exigua, Mamestra brassicae, Panolis flammea, Prodenia litura, Spodoptera* spec., *Trichoplusia ni, Carpocapsa pomonella, Pieris* spec., *Chilo* spec., *Pyrausta nubilalis, Ephestia kuhniella, Galleria mellonella, Cacoecia podana, Capua reticulana, Choristoneura fumiferana, Clysia ambiguella, Homona magnanima* and *Tortrix viridana;* from the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spec., *Psylliodes chrysocephala, Epilachna varivestis, Atomaria* spec., *Oryzaephilus surinamensis, Anthonomus* spec., *Sitophilus* spec., *Otiorrhynchus sulcatus, Cosmopolites sordidus, Ceuthorrhynchus assimilis, Hypera postica, Dermestes* spec., *Trogoderma* spec., *Anthrenus* spec., *Attagenus* spec., *Lyctus* spec., *Meligethes aeneus, Ptinus* spec., *Niptus hololeucus, Gibbium psylloides, Tribolium* spec., *Tenebrio molitor, Agriotes* spec., *Conoderus* spec., *Melolontha melolontha, Amphimallus solstitialis* and *Costelytra zealandica; from the order of the Hymenoptera, for example, Diprion* spec., *Hoplocampa* spec., *Lasius* spec., *Monomorium pharaonis* and *Vespa* spec., from the order of the Diptera, for example, *Aedes* spec., *Anophelas* spec., *Culex* spec., *Drosophila melanogaster, Musca domestica, Fannia* spec., *Stomoxys calcitrans, Hypoderma* spec., *Bibio hortulanus, Oscinella* frit, *Phorbia* spec., *Pegomyia hyoscyami, Calliphora erythrocephala, Lucilia* spec., *Chrysomyia* spec., *Ceratitis capitata, Dacus oleae* and *Tipula paludosa;* and from the order of the Siphonaptera, for example *Xenopsylla cheopis.*

The active compounds according to the invention can be used to combat nematodes, especially phytophathogenic nematodes. These essentially include leaf nematodes (Arphelenchoides), such as the chrysanthemum eelworm (*A. ritzemabosi*), the leaf-blotch eelworm (*A. fragariae*) and the rice eelworm (*A. oryzae*); stem nematodes (Ditylenchus), such as the stem eelworm (*D. Dipsaci*); root-knot nematodes (Meloidogyne), such as *M. arenaria* and *M. incognita;* cystforming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

When used against pests harmful to health and pests of stored products, the active compounds are distinguished by an excellent residual action on wood and clay, as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g., conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as Freon; inert dispersible liquid diluent carriers, including inert organic solvents, such as aromatic hydrocarbons (e.g., benzene, toluene, xylene, alkyl naphthalenes, etc.), halogenated, especially chlorinated, aromatic hydrocarbons (e.g., chlorobenzenes, etc.), cycloalkanes, (e.g., cyclohexane, etc.), paraffins (e.g., petroleum or mineral oil fractions), chlorinated aliphatic hydrocarbons (e.g., methylene chloride, chloroethylenes, etc.), alcohols (e.g., methanol, ethanol, propanol, butanol, glycol, etc.) as well as ethers and esters thereof (e.g., glycol monomethyl ether, etc.), amines (e.g., ethanolamine, etc.), amides (e.g., dimethyl formamide, etc.), sulfoxides (e.g., dimethyl sulfoxide, etc.), acetonitrile, ketones (e.g., acetone, methyl ethyl ketone, methyl isobutyl ketone, cyclohexanone, etc.), and/or water; as well as inert dispersible finely divided solid carriers, such as ground natural minerals (e.g., kaolins, clays, alumina, silica, chalk, i.e., calcium carbonate, talc, attapulgite, montmorillonite, kieselguhr, etc.) and ground synthetic minerals (e.g., highly dispersed silicic acid, silicates, e.g., alkali silicates, etc.); whereas the following may be chiefly considered for use as conventional carrier vehicle assistants, e.g., surface-active agents, for this purpose: emulsifying agents, such as non-ionic and/or anionic emulsifying agents (e.g., polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other arthropodicides and nematicides, or fungicides, bactericides, rodenticides, herbicides, fertilizers, growth-regulating agents, etc., if desired, or in the form of particular dosage preparations for specific application made therefrom, such as solutions, emulsions, wettable powders, suspensions, powders, dusting agents, foams, pastes, soluble powders, granules, aerosols, suspension-emulsions, concentrates, seedtreatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV (ultra-low-volume) cold mist and warm mist formulations.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g., a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g., average particle diameter of from 50–100 microns, or even less, i.e., mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g., about 20–100% by weight of the active compound.

When uaed against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g., arthropods and nematodes, and more particularly methods of combating insects, acarids and nematodes, which comprises applying to at least one of correspondingly (a) such arthropods, (b) such nematodes, and (c) the corresponding habitat thereof, i.e., the locus to be protected, e.g., to a growing crop, to an area where a crop is to be grown or to a domestic animal, a correspondingly combative or toxic amount, i.e., an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Drosophila test

Solvent: 3 parts by weight of acetone
Emulsifier: 1 part by weight of alkylarly polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% means that all the flies were killed; 0% means that no flies were killed.

The active compounds, the concentrations of the active compounds, the evaluation times and the results can be seen from the following table:

Table 1

(Drosophila Test)

| Active compound | | Active compound concentration in % | Degree of destruction in % after 1 day |
|---|---|---|---|
| $CH_3-NH-CO-\underset{\underset{CH_3}{\|}}{CH}-S-C_2H_4-S-\overset{\overset{O}{\|\|}}{P}(OCH_3)_2$ (known) | (A) | 0.1 | 0 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}(OCH_3)_2$ | (2) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{C_2H_5}{\overset{OCH_3}{\diagup}}$ | (3) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{O}{\|\|}}{P}\underset{NH_2}{\overset{OCH_3}{\diagup}}$ | (6) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}(OC_2H_5)_2$ | (12) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{C_2H_5}{\overset{OC_2H_5}{\diagup}}$ | (1) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{OC_3H_7i}{\overset{CH_3}{\diagup}}$ | (4) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{C_2H_5}{\overset{OC_3H_7}{\diagup}}$ | (7) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{OC_2H_5}{\overset{SC_3H_7}{\diagup}}$ | (8) | 0.1 | 100 |
| $\underset{F}{\overset{Cl}{\diagdown}}CH-\underset{\underset{F}{\|}}{\overset{\overset{F}{\|}}{C}}-S-C_2H_4-S-\overset{\overset{S}{\|\|}}{P}\underset{NH-C_3H_7i}{\overset{OC_2H_5}{\diagup}}$ | (10) | 0.1 | 100 |

EXAMPLE 2

Plutella test

Solvent: 3 parts by weight of acetone
Emulsifier: 1 part by weight of alkylaryl polyglycol ether To produce a suitable preparation of active compound 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and when then infested with caterpillars of the diamond-back moth (Plutella maculipennis).

After the specified periods of time, the degree of destruction was determined as a percentage: 100% means that all the caterpillars were killed, whereas 0% means that none of the caterpillars were killed.

The active compounds, the concentrations of the active compounds, the evaluation times and the results can be seen from the following table:

Table 2

(Plutella test)

| Active compound | | Active compound concentration in % | Degree of destruction in % after 3 days |
|---|---|---|---|
| $CH_3-NH-CO-\underset{\underset{CH_3}{\|}}{CH}-S-C_2H_4-S-\overset{\overset{O}{\|\|}}{P}(OCH_3)_2$ | (A) | 0.1 | 0 |

Table 2-continued

| Active compound | (Plutella test) | Active compound concentration in % | Degree of destruction in % after 3 days |
|---|---|---|---|
| Cl\CH—CF₂—S—C₂H₄—S—P(S)(OCH₃)₂ (with F on C) | (2) | 0.1 | 100 |
| Cl\CH—CF₂—S—C₂H₄—S—P(S)(OCH₃)(C₂H₅) | (3) | 0.1 | 100 |
| Cl\CH—CF₂—S—C₂H₄—S—P(O)(OCH₃)(NH₂) | (6) | 0.1 | 100 |
| Cl\CH—CF₂—S—C₂H₄—S—P(S)(OC₂H₅)₂ | (12) | 0.1 | 100 |
| Cl\CH—CF₂—S—C₂H₄—S—P(S)(OC₂H₅)(C₂H₅) | (1) | 0.1 | 100 |
| Cl\CH—CF₂—S—C₂H₄—S—P(S)(CH₃)(OC₃H₇i) | (4) | 0.1 | 100 |
| Cl\CH—CF₂—S—C₂H₄—S—P(S)(OC₃H₇)(C₂H₅) | (7) | 0.1 | 100 |
| Cl\CH—CF₂—S—C₂H₄—S—P(S)(SC₃H₇)(OC₂H₅) | (8) | 0.1 | 100 |
| Cl\CH—CF₂—S—C₂H₄—S—P(S)(OC₂H₅)(NH—C₃H₇i) | (10) | 0.1 | 100 |

EXAMPLE 3

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 3

| Active compound | (Myzus test) | Active compound concentration in % | Degree of destruction in % after 1 day |
|---|---|---|---|
| CH₃—NH—CO—CH(CH₃)—S—C₂H₄—S—P(O)(OCH₃)₂ (known) | (A) | 0.1<br>0.01<br>0.001 | 100<br>70<br>0 |

Table 3-continued

| | (Myzus test) | | |
|---|---|---|---|
| Active compound | | Active compound concentration in % | Degree of destruction in % after 1 day |
| $\text{Cl}\diagdown\phantom{x}\text{F}\phantom{xxxxx}\text{O}\phantom{x}\text{OCH}_3$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{NH}_2$ | (6) | 0.1<br>0.01<br>0.001 | 100<br>100<br>99 |
| $\text{Cl}\diagdown\phantom{x}\text{F}\phantom{xxxxx}\text{S}$ $\phantom{xx}\text{CH}-\text{C}-\text{S}-\text{C}_2\text{H}_4-\text{S}-\text{P}(\text{OC}_2\text{H}_5)_2$ $\text{F}\diagup\phantom{x}\text{F}$ | (12) | 0.1<br>0.01<br>0.001 | 100<br>99<br>95 |
| $\text{Cl}\diagdown\phantom{x}\text{F}\phantom{xxxxx}\text{S}\phantom{x}\text{OC}_2\text{H}_5$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{C}_2\text{H}_5$ | (1) | 0.1<br>0.01<br>0.001 | 100<br>100<br>80 |
| $\text{Cl}\diagdown\phantom{x}\text{F}\phantom{xxxxx}\text{S}\phantom{x}\text{OC}_3\text{H}_7$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{C}_2\text{H}_5$ | | 0.01<br>0.01<br>0.001 | 100<br>100<br>95 |

EXAMPLE 4

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed whereas 0% means that none of the spider mites were killed.

The active compounds, the concentrations of the active compounds, the evaluation times and the results can be seen from the following table:

Table 4

| | (Tetranychus test) | | |
|---|---|---|---|
| Active compound | | Active compound concentration in % | Degree of destruction in % after 2 days |
| $\phantom{xxxxx}\text{CH}_3\phantom{xxxxx}\text{O}$ $\text{CH}_3-\text{NH}-\text{CO}-\text{CH}-\text{S}-\text{C}_2\text{H}_4-\text{S}-\text{P}(\text{OCH}_3)_2$<br>(known) | (A) | 0.1 | 0 |
| $\text{Cl}\diagdown\phantom{x}\text{F}\phantom{xxxxx}\text{O}\phantom{x}\text{OCH}_3$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{NH}_2$ | (6) | 0.1 | 100 |
| $\text{Cl}\diagdown\phantom{x}\text{F}\phantom{xxxxx}\text{S}\phantom{x}\text{SC}_3\text{H}_7$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{OC}_2\text{H}_5$ | (8) | 0.1 | 100 |
| $\text{Cl}\diagdown\phantom{x}\text{F}\phantom{xxxxx}\text{S}\phantom{x}\text{OC}_2\text{H}_5$ $\phantom{xx}\text{CH}-\text{C}-\text{S}-\text{C}_2\text{H}_4-\text{S}-\text{P}$ $\text{F}\diagup\phantom{x}\text{F}\phantom{xxxxxxxx}\text{NH}-\text{C}_3\text{H}_7\text{i}$ | (10) | 0.1 | 90 |

EXAMPLE 5

Critical Concentration test/soil insects

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/1). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness was 100% if all the test insects had been killed and was 0% if exactly as many test insects were still alive as in the case of the untreated control.

The active compounds, amounts used and results can be seen from the table which follows:

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which was quoted in ppm (= mg/1). The soil was filled into pots and the pots were left to stand at room temperature.

Table 5

(Soil insecticide test/*Phorbia antiqua* grubs in the soil)

| Active compound | | Degree of destruction in % at an active compound concentration of 10 ppm |
|---|---|---|
| $C_2H_5-S-C_2H_4-S-P(=S)(OC_2H_5)(OC_2H_5)$ (known) | (B) | 0 |
| $Cl(F)(F)CH-C(F)-S-C_2H_4-S-P(=S)(OC_2H_5)(C_2H_5)$ | (1) | 100 |
| $Cl(F)(F)CH-C(F)-S-C_2H_4-S-P(=S)(OCH_3)_2$ | (2) | 100 |
| $Cl(F)(F)CH-C(F)-S-C_2H_4-S-P(=S)(OCH_3)(C_2H_5)$ | (3) | 100 |
| $Cl(F)(F)CH-C(F)-S-C_2H_4-S-P(=S)(CH_3)(OC_3H_7-i)$ | (4) | 100 |
| $Cl(F)(F)CH-C(F)-S-C_2H_4-S-P(=S)(OC_3H_7)(C_2H_5)$ | (7) | 100 |
| $Cl(F)(F)CH-C(F)-S-C_2H_4-S-P(=S)(SC_3H_7)(OC_2H_5)$ | (8) | 100 |
| $Cl(F)(F)CH-C(F)-S-C_2H_4-S-P(=S)(OC_2H_5)(NH-CH(CH_3)_2)$ | (10) | 100 |
| $Cl(F)(F)CH-C(F)-S-C_2H_4-S-P(=S)(OC_2H_5)_2$ | (12) | 100 |

EXAMPLE 6

Critical concentration test/soil insects
Test insect: *Tenebrio molitor* larvae in the soil
Solvent: 3 parts by weight of acetone After 24 hours the test insects were introduced into the treated soil and after a further 2 to 7 days the degree of effectiveness of the active compound was determined in % by counting the dead and live test insects. The degree of effectiveness was 100% if all the test insects had been killed and is 0% if exactly as many test insects were still alive as in the case of the untreated control.

The active compounds, amounts used and the results can be seen from the table which follows:

Table 6

(Soil insecticide test/*Tenebrio molitor* larvae in the soil)

| Active compound | | Degree of destruction in % at an active compound concentration of 10 ppm |
|---|---|---|
| $C_2H_5-S-C_2H_4-S-\overset{S}{\overset{\|}{P}}\underset{OC_2H_5}{\overset{OC_2H_5}{\diagup}}$ (known) | (B) | 0 |
| $\underset{F}{\overset{Cl}{\diagdown}}CH-\underset{F}{\overset{F}{\underset{\|}{C}}}-S-C_2H_4-S-\overset{S}{\overset{\|}{P}}(OC_2H_5)_2$ | (1) | 100 |
| $\underset{F}{\overset{Cl}{\diagdown}}CH-\underset{F}{\overset{F}{\underset{\|}{C}}}-S-C_2H_4-S-\overset{S}{\overset{\|}{P}}\underset{C_2H_5}{\overset{OCH_3}{\diagup}}$ | (3) | 100 |
| $\underset{F}{\overset{Cl}{\diagdown}}CH-\underset{F}{\overset{F}{\underset{\|}{C}}}-S-C_2H_4-S-\overset{S}{\overset{\|}{P}}\underset{OC_3H_7-i}{\overset{CH_3}{\diagup}}$ | (4) | 100 |
| $\underset{F}{\overset{Cl}{\diagdown}}CH-\underset{F}{\overset{F}{\underset{\|}{C}}}-S-C_2H_4-S-\overset{S}{\overset{\|}{P}}\underset{C_2H_5}{\overset{OC_3H_7}{\diagup}}$ | (7) | 100 |
| $\underset{F}{\overset{Cl}{\diagdown}}CH-\underset{F}{\overset{F}{\underset{\|}{C}}}-S-C_2H_4-S-\overset{S}{\overset{\|}{P}}\underset{OC_2H_5}{\overset{SC_3H_7}{\diagup}}$ | (8) | 100 |
| $\underset{F}{\overset{Cl}{\diagdown}}CH-\underset{F}{\overset{F}{\underset{\|}{C}}}-S-C_2H_4-S-\overset{S}{\overset{\|}{P}}(OC_2H_5)_2$ | (12) | 100 |

EXAMPLE 7

Critical concentration test/nematodes
Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance, only the amount of active compound per unit volume of soil, which was given in ppm, was decisive. The soil was filled into pots, lettuce was sown in and the pots were kept at a greenhouse temperature of 27° C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 7

(Nematicide Test/*Meloidogyne incognita*)

| Active compound | Degree of destruction in % at an active compound concentration of 10 ppm |
|---|---|
| $C_2H_5-S-C_2H_4-S-\overset{S}{\overset{\|}{P}}\underset{OC_2H_5}{\overset{OC_2H_5}{\diagup}}$ (known)  B) | 0 |

Table 7-continued (Nematicide Test/*Meloidogyne incognita*)

| Active compound | Degree of destruction in % at an active compound concentration of 10 ppm |
|---|---|
| (1) Cl\\CH−C(F)(F)−S−C$_2$H$_4$−S−P(=S)(OC$_2$H$_5$)(C$_2$H$_5$) with CHF on left | 100 |
| (3) Cl\\CH(F)−C(F)(F)−S−C$_2$H$_4$−S−P(=S)(OCH$_3$)(C$_2$H$_5$) | 100 |
| (4) Cl\\CH(F)−C(F)(F)−S−C$_2$H$_4$−S−P(=S)(CH$_3$)(OC$_3$H$_7$−i) | 100 |
| (10) Cl\\CH(F)−C(F)(F)−S−C$_2$H$_4$−S−P(=S)(OC$_2$H$_5$)(NH−C$_3$H$_7$i) | 100 |
| (12) Cl\\CH(F)−C(F)(F)−S−C$_2$H$_4$−S−P(=S)(OC$_2$H$_5$)$_2$ | 100 |

EXAMPLE 8

LT$_{100}$ test for Diptera
Test insect: *Musca domestica*
Solvent: acetone 2 parts by weight of active compound were dissolved in 1000 parts by volume of solvent. The solution so obtained was diluted with further solvent to the desired lower concentrations.

2.5 ml of the solution of active compound was pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound used. About 25 test insects were then placed in the Petri dish and it was covered with a glass lid.

The condition of the test insects was continuously observed. The time which was necessary for a 100% knock down effect was determined.

The test insects, the active compounds, the concentrations of the active compounds and the periods of time at which there is a 100% knock down effect can be seen from the following table:

Table 8

(LT$_{100}$ Test for *Diptera/Musca domestica*)

| Active compound | | Active compound concentration of the solution in % | LT$_{100}$ (') in minutes or (hrs) in hours |
|---|---|---|---|
| CH$_3$−NH−CO−CH(CH$_3$)−S−C$_2$H$_4$−S−P(=O)(OCH$_3$)$_2$ (known) | (A) | 0.2 | 8$^{hrs}$ = 20% |
| Cl\\CH(F)−C(F)(F)−S−C$_2$H$_4$−S−P(=O)(OC$_2$H$_5$)$_2$ | (5) | 0.2<br>0.02 | 130'<br>6$^{hrs}$ = 60% |
| Cl\\CH(F)−C(F)(F)−S−C$_2$H$_4$−S−P(=S)(OCH$_3$)$_2$ | (2) | 0.2<br>0.02<br>0.002 | 155'<br>240'<br>6$^{hrs}$ = 70% |
| Cl\\CH(F)−C(F)(F)−S−C$_2$H$_4$−S−P(=S)(OC$_2$H$_5$)$_2$ | (12) | 0.2<br>0.02<br>0.002 | 60'<br>120'<br>6$^{hrs}$ |

Table 8-continued (LT$_{100}$ Test for *Diptera/Musca domestica*)

| Active compound | | Active compound concentration of the solution in % | LT$_{100}$ (') in minutes or (hrs) in hours |
|---|---|---|---|
| Cl\\CH—C(F)(F)—S—C$_2$H$_4$—S—P(=S)(OC$_2$H$_5$)(C$_2$H$_5$) | (1) | 0.2<br>0.02<br>0.002 | 65'<br>110'<br>6$^{hrs}$ |
| Cl\\CH—C(F)(F)—S—C$_2$H$_4$—S—P(=S)(OCH$_3$)(C$_2$H$_5$) | (3) | 0.2<br>0.02<br>0.002 | 65'<br>100'<br>6$^{hrs}$ |
| Cl\\CH—C(F)(F)—S—C$_2$H$_4$—S—P(=S)(CH$_3$)(OC$_3$H$_7$i) | (4) | 0.2<br>0.02<br>0.002 | 100'<br>180'<br>6$^{hrs}$ = 60% |
| Cl\\CH—C(F)(F)—S—C$_2$H$_4$—S—P(=S)(OC$_3$H$_7$)(C$_2$H$_5$) | (7) | 0.2<br>0.02 | 80'<br>190' |

EXAMPLE 9

LD$_{100}$ test

Test insects: *Sitophilus granarius*

Solvent: Acetone 2 parts by weight of the active compound were dissolved in 1,000 parts by volume of the solvent. The solution so obtained was diluted with further solvent to the desired concentration.

2.5 ml of the solution of the active compound were pipetted into a Petri dish. On the bottom of the Petri dish there was a filter paper with a diameter of about 9.5 cm. The Petri dish remained uncovered until the solvent had completely evaporated. The amount of active compound per m$^2$ of filter paper varied with the concentration of the solution of active compound. About 25 test insects were then placed in the Petri dish and it was covered with a glass lid.

The condition of the test insects were observed 3 days after the commencement of the experiments. The destruction, in %, was determined.

The active compounds, the concentrations of the active compounds, the test insects and the results can be seen from the following table:

Table 9

(LD$_{100}$ Test/*Sitophilus granarius*)

| Active compound | Active compound concentration of the solution in % | Degree of destruction in % |
|---|---|---|
| CH$_3$—NH—CO—CH(CH$_3$)—S—C$_2$H$_4$—S—P(=O)(OCH$_3$)$_2$ (known) (A) | 0.2 | 30 |
| Cl\\CH—C(F)(F)—S—C$_2$H$_4$—S—P(=O)(OCH$_3$)(NH$_2$) (6) | 0.2<br>0.02 | 100<br>40 |
| Cl\\CH—C(F)(F)—S—C$_2$H$_4$—S—P(=S)(OCH$_3$)$_2$ (2) | 0.2<br>0.02 | 100<br>100 |
| Cl\\CH—C(F)(F)—S—C$_2$H$_4$—S—P(=S)(OC$_2$H$_5$)$_2$ (12) | 0.2<br>0.02 | 100<br>100 |
| Cl\\CH—C(F)(F)—S—C$_2$H$_4$—S—P(=S)(OC$_2$H$_5$)(C$_2$H$_5$) (1) | 0.2<br>0.02 | 100<br>100 |
| Cl\\CH—C(F)(F)—S—C$_2$H$_4$—S—P(=S)(OCH$_3$)(C$_2$H$_5$) (3) | 0.2<br>0.02<br>0.002 | 100<br>100<br>50 |

Table 9-continued

| (LD₁₀₀ Test/*Sitophilus granarius*) | | |
|---|---|---|
| Active compound | Active compound concentration of the solution in % | Degree of destruction in % |
| 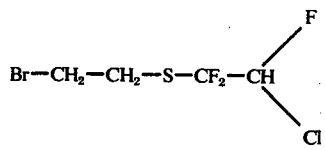 (4) | 0.2<br>0.02 | 100<br>100 |
| (7) | 0.2<br>0.02 | 100<br>100 |
| (8) | 0.2<br>0.02 | 100<br>100 |

The process of this invention is illustrated by the following preparative Examples.

EXAMPLE 10 a. The starting material was prepared, for example, as follows:

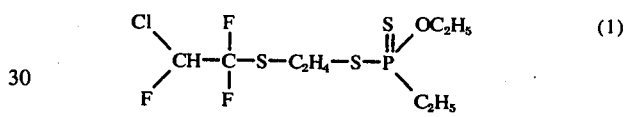

9.6 g (0.035 mole) of phosphorus tribromide were added dropwise, without cooling, to a solution of 19.5 g (0.1 mole) of 1,1,2-trifluoro-2-chloro-2'-hydroxy-diethylsulfide (prepared according to K. E. Rapp et al., J. Amer. Chem. Soc. 72 (1950), page 3644) in 100 ml of ethylene chloride. The mixture was stirred for a further half-hour at 50° C and was cooled to room temperature and then washed with 100 ml of ice water. The organic phase was dried over sodium sulfate. The solvent was then distilled off. The residue was distilled under reduced pressure. This gave 10.7 (41% of theory) of 1,1,2-trifluoro-2-chloro-2'-bromodiethyl thioether in the form of a colorless liquid of boiling point 76° C/14 mm Hg, and with refractive index $n_D^{23}$ of 1.4713.

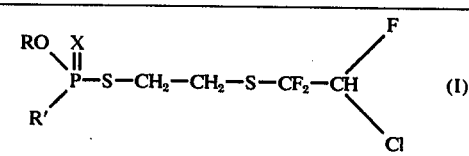

A mixture of 25.7 g (0.1 mole) of 1,1,2-trifluoro-2-chloro-2'-bromodiethyl thioether, 200 ml of acetonitrile and 20.8 g (0.1 mole) of the potassium salt of O-ethylethanethionothiolphosphonic acid ester was stirred for 2 hours at 45° C. 400 ml of toluene were then added and the mixture was washed twice with 300 ml of water at a time. The organic phase was dried over sodium sulfate and freed from the solvent under reduced pressure, and the residue was subjected to slight distillation. This gave 21.1 g (61% of theory) of O-ethylethane-S-[2-(1',1',2'-trifluoro-2'-chloroethylmercapto)-ethyl]-thionothiolphosphonic acid ester in the form of a yellow oil having a refractive index $n_D^{25}$ of 1.5169.

The following compounds could be prepared analogously:

$$\begin{array}{c} RO \\ \diagdown \\ R' \end{array} \overset{X}{\underset{\|}{P}} -S-CH_2-CH_2-S-CF_2-CH \begin{array}{c} F \\ \diagup \\ \diagdown \\ Cl \end{array} \quad (I)$$

| Compound No. | R | R' | X | Yield (% of theory) | Physical data (refractive index) |
|---|---|---|---|---|---|
| 2 | CH₃— | CH₃O— | S | 67 | $n_D^{25}$:1.5050 |
| 3 | CH₃— | C₂H₅— | S | 92 | $n_D^{25}$:1.5237 |
| 4 | iso—C₃H₅— | CH₃— | S | 82 | $n_D^{25}$:1.5145 |
| 5 | C₂H₅— | C₂H₅O— | O | 44 | $n_D^{26}$:1.4718 |
| 6 | CH₃— | NH₂— | O | 45 | $n_D^{22}$:1.5113 |
| 7 | n—C₃H₇— | C₂H₅— | S | 83 | $n_D^{22}$:1.5153 |

-continued

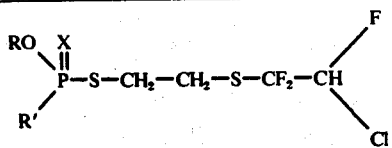

| Compound No. | R | R' | X | Yield (% of theory) | Physical data (refractive index) |
|---|---|---|---|---|---|
| 8 | $C_2H_5$ | n—$C_3H_6S$— | S | 81 | $n_D^{22}$:1.5260 |
| 9 | $C_2H_5$— | ⟨phenyl⟩ | S | 76 | $n_D^{23}$:1.5552 |
| 10 | $C_2H_5$— | iso—$C_3H_7$—NH— | S | 80 | $n_D^{23}$:1.5114 |
| 11 | iso—$C_3H_7$— | iso—$C_3H_7O$— | S | 87 | $n_D^{22}$:1.4950 |
| 12 | $C_2H_5$— | $C_2H_5O$— | S | 77 | $n_D^{22}$:1.5139 |

Other compounds which can be similarly prepared include:

| Compound No. | R | R' | X |
|---|---|---|---|
| 13 | $C_2H_5$ | n—$C_3H_7$— | S |
| 14 | sec.—$C_4H_9$— | tert.—$C_4H_9$— | S |
| 15 | n—$C_5H_{11}$— | n—$C_5H_{11}O$— | S |
| 16 | $CH_3$— | $CH_3S$— | O |
| 17 | iso—$C_3H_7$— | n—$C_5H_{11}NH$— | O | and the like.

It will be appreciated that the instant specification and examples are set forth by way of illustration and not limitation, and that various modifications and changes may be made without departing from the spirit and scope of the present invention.

What is claimed is:

1. An O-alkyl-S-[2-(1',1',2'-trifluoro-2'-chloroethylmercapto)-ethyl](thiono)(di)thiolphosphoric(phosphonic) acid ester or ester-amide of the formula

in which
R is alkyl with 1 to 6 carbon atoms,
R' is alkyl, alkoxy, alkylmercapto or alkylamino with 1 to 6 carbon atoms in each alkyl moiety, amino or phenyl, and
X is oxygen or sulfur.

2. A compound according to claim 1, in which R is straight-chain or branched alkyl with up to 5 carbon atoms, and R' is straight-chain or branched alkyl, alkoxy, alkylmercapto or alkylamino with up to 5 carbon atoms in each alkyl moiety, amino or phenyl.

3. The compound according to claim 1, wherein such compound is O-ethylethane-S-[2-(1',1',2'-trifluoro-2'-chloroethylmercapto)-ethyl]-thionothiolphosphonic acid ester of the formula

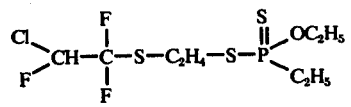

4. The compound according to claim 1, wherein such compound is O-methylethane-S-[2-(1',1',2'-trifluoro-2'-chloroethylmercapto)-ethyl]-thionothiolphosphonic acid ester of the formula

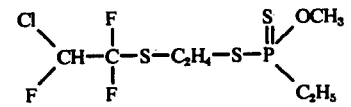

5. The compound according to claim 1, wherein such compound is O-isopropylmethane-S-[2-(1',1',2'-trifluoro-2'-chloroethylmercapto)-ethyl]-thionothiolphosphonic acid ester of the formula

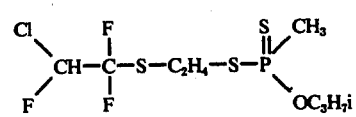

6. The compound according to claim 1, wherein such compound is O-n-propylethane-S-[2-(1',1',2'-trifluoro-2'-chloroethylmercapto)-ethyl]-thionothiolphosphonic acid ester of the formula

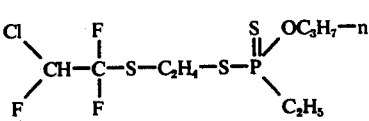

7. The compound according to claim 1, wherein such compound is O-ethyl-S-n-propyl-S-[2-(1',1',2'-trifluoro-2'-chloroethylmercapto)-ethyl]-thionodithiolphosphoric acid ester of the formula

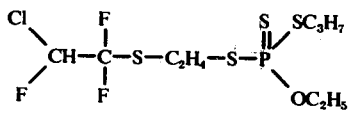

8. An arthropodicidal or nematicidal composition containing as active ingredient an arthropodicidally or nematicidally effective amount of a compound according to claim 1 in admixture with a diluent.

9. A method or combating arthropod or nematode pests which comprises applying to the pests or to a habitat thereof an arthropodically or nematicidally effective amount of a compound according to claim 1.

10. The method according to claim 9 in which said compound is

O-ethylethane-S-[2-(1',1',2'-trifluoro-2'-chloroethylmercapto)-ethyl]-thionothiolphosphonic acid ester, O-methylethane-S-[2-(1',1',2'-trifluoro-2'-chloroethylmercapto)-ethyl]-thionothiolphosphonic acid ester, O-isopropylmethane-S-[2-(1',1',2'-trifluoro-2'-chloroethylmercapto)-ethyl]-thionothiolphosphonic acid ester, O-n-propylethane-S-[2-(1',1',2'-trifluoro-2'-chloroethylmercapto)-ethyl]-thionothiolphosphonic acid ester or O-ethyl-S-n-propyl-S-[2-(1',1',2'-trifluoro-2'-chloroethylmercapto)-ethyl]-thionodithiolphosphoric acid ester.

* * * * *